United States Patent [19]
Clark et al.

[11] Patent Number: 6,143,352
[45] Date of Patent: Nov. 7, 2000

[54] PH-MODIFIED BIOCOMPATIBLE MONOMER AND POLYMER COMPOSITIONS

[75] Inventors: Jeffrey G. Clark; Jeffrey C. Leung, both of Raleigh, N.C.

[73] Assignee: Closure Medical Corporation, Raleigh, N.C.

[21] Appl. No.: 08/714,288

[22] Filed: Sep. 18, 1996

Related U.S. Application Data

[63] Continuation of application No. 08/266,647, Jun. 28, 1994, abandoned.

[51] Int. Cl.$^7$ .................................................... B05D 3/00
[52] U.S. Cl. .................... 427/2.1; 156/331.2; 424/78.06; 424/78.35; 523/118; 523/202; 523/205; 523/210; 526/298
[58] Field of Search .......................... 156/331.2; 427/2.1; 526/298; 523/118, 202, 205, 210; 424/78.35, 487, 78.06; 604/214

[56] References Cited

U.S. PATENT DOCUMENTS

| | | |
|---|---|---|
| 2,439,081 | 4/1948 | Dickey et al. . |
| 2,721,858 | 10/1955 | Joyner et al. . |
| 2,751,314 | 6/1956 | Keil . |
| 2,765,332 | 10/1956 | Coover, Jr. et al. . |
| 2,798,063 | 7/1957 | Fowler . |
| 2,885,374 | 5/1959 | Sweeney . |
| 2,956,884 | 10/1960 | Caldwell . |
| 2,982,749 | 5/1961 | Friedrich et al. . |
| 3,030,951 | 4/1962 | Mandarino . |
| 3,223,083 | 12/1965 | Cobey . |
| 3,254,111 | 5/1966 | Hawkins et al. . |
| 3,321,435 | 5/1967 | Fritz et al. . |
| 3,404,122 | 10/1968 | Fritz et al. . |
| 3,483,870 | 12/1969 | Coover et al. ........................ 424/78.06 |
| 3,527,841 | 9/1970 | Wicker et al. ............................ 526/298 |
| 3,554,990 | 1/1971 | Quinn et al. . |
| 3,559,652 | 2/1971 | Banitt et al. ............................. 526/298 |
| 3,564,078 | 2/1971 | Wicker, Jr. et al. . |
| 3,591,676 | 7/1971 | Hawkins et al. . |
| 3,667,472 | 6/1972 | Halpern . |
| 3,691,090 | 9/1972 | Kitajima et al. ........................ 523/205 |
| 3,716,502 | 2/1973 | Loew . |
| 3,722,599 | 3/1973 | Robertson et al. . |
| 3,728,375 | 4/1973 | Coover, Jr. et al. . |
| 3,759,260 | 9/1973 | Nolan et al. . |
| 3,759,264 | 9/1973 | Coover, Jr. et al. . |
| 3,839,272 | 10/1974 | Yankowsky . |
| 3,896,077 | 7/1975 | Leonard et al. . |
| 3,909,408 | 9/1975 | Ishida et al. . |
| 3,919,383 | 11/1975 | Yankowsky . |
| 3,940,362 | 2/1976 | Overhults . |
| 3,951,903 | 4/1976 | Shaffer . |
| 3,995,641 | 12/1976 | Kronenthal et al. . |
| 4,032,993 | 7/1977 | Coquard et al. . |
| 4,042,442 | 8/1977 | Dombroski et al. . |
| 4,127,382 | 11/1978 | Perry . |
| 4,196,271 | 4/1980 | Yamada et al. ........................ 526/298 |

(List continued on next page.)

FOREIGN PATENT DOCUMENTS

| | | |
|---|---|---|
| 1162904 | 2/1984 | Canada . |
| 0138448 | 4/1985 | European Pat. Off. . |
| 0543499 | 5/1993 | European Pat. Off. . |
| 1669142 | 5/1971 | Germany . |
| 48-95428 | 12/1973 | Japan . |
| 57-50541 | 3/1982 | Japan . |
| 63-11166 | 1/1988 | Japan . |
| 5-123329 | 5/1993 | Japan . |
| 840072 | 6/1981 | U.S.S.R. . |
| 1057014 | 2/1967 | United Kingdom . |
| 1196049 | 11/1967 | United Kingdom . |
| 1146117 | 3/1969 | United Kingdom . |
| 1 196 049 | 6/1970 | United Kingdom . |
| 1507739 | 4/1978 | United Kingdom . |

OTHER PUBLICATIONS

"Methods of Abating Residual Formaldehyde in Industrial Resins," EPO Applied Technology Series vol. 10.

R.S. Perry et al., "A Search for Potential Formaldehyde Acceptors," vol. 12, No. 12, pp. 311–316, 1980.

S.B. Aronson et al., "Toxicity of the Cyanoacrylates," Arch Ophthal, vol. 84, pp.342–348, 1970.

R.E. Silva Jr., et al., "Carbohydrazide Found to be an Effectivea Scavenger for Reducing Free Formaldehyde," 1980 Intersectional Technical Paper Competition, AATCC Technical Manual, vol. 13, pp. 29–39, 1981.

"Methods of Abating Residual Formaldehyde in Industrial Resins," EPO Applied Technology Series vol. 10. Not Submitted.

W.R. Vezin et al., "In vitro Heterogeneous Degradation of poly (n–alkyl α–cyanoacrylate," Journal of Biomedical Materials Research, vol. 14, pp. 93–106, 1980.

S.C. Woodward et al., "Histotoxicity of Cyanoacrylate Tissue Adhesive in the Rat," Annals of Surgery, vol. 162, pp. 113–122, 1965.

F.J. Papatheofanis, "Cystotoxity of alkyl–2–cyanacrylate Adhesives," Journal of Biomedical Materials Research, vol.23, pp. 661–668, 1989.

C. Tomasino et al., "Evluation of Formaldehyde Scavengers," vol. 16, No. 12, pp. 259–265, 1964.

C.A. Carton et al., "Experimental Studies in the Surgery of Small Blood Vessels, IV. Nonsuture Anastomosis of Arteries and Veins, Using Flanged Ring Protheses and Plastic Adhesive," Surgical Forum, vol. 11 (1960) pp. 238–239.

(List continued on next page.)

Primary Examiner—John J. Gallagher
Attorney, Agent, or Firm—Oliff & Berridge, PLC

[57] ABSTRACT

The pH-modified monomer and polymer compositions are useful as biomedical and surgical adhesives, sealants, implants and bioactive agent release carriers or matrices. They comprise a monomer or polymer; and an effective amount of an acidic or basic pH modifier effective to modify the pH of an immediate in vivo environment of the composition to a pH range at which the polymer biodegrades at a different rate than at physiologic pH. The invention also relates to in vivo applications in which surfaces are joined or treated with such pH-modified biocompatible compositions.

50 Claims, No Drawings

U.S. PATENT DOCUMENTS

| | | |
|---|---|---|
| 4,278,785 | 7/1981 | Rosenfeld . |
| 4,297,160 | 10/1981 | Kusayama et al. . |
| 4,364,876 | 12/1982 | Kimura et al. . |
| 4,374,226 | 2/1983 | Sivaramakrishnan . |
| 4,374,953 | 2/1983 | Chou et al. . |
| 4,413,069 | 11/1983 | Marshall .................................. 523/210 |
| 4,479,933 | 10/1984 | Akimova et al. .................... 424/78.35 |
| 4,490,515 | 12/1984 | Mariotti et al. . |
| 4,524,093 | 6/1985 | Devry . |
| 4,578,061 | 3/1986 | Lemelson . |
| 4,582,648 | 4/1986 | Hirakawa . |
| 4,675,273 | 6/1987 | Woods et al. . |
| 4,744,364 | 5/1988 | Kensey . |
| 4,804,691 | 2/1989 | English et al. . |
| 4,832,688 | 5/1989 | Sagae et al. . |
| 4,852,568 | 8/1989 | Kensey . |
| 4,890,612 | 1/1990 | Kensey . |
| 4,891,225 | 1/1990 | Langer et al. . |
| 4,900,303 | 2/1990 | Lemelson . |
| 5,021,059 | 6/1991 | Kensey et al. . |
| 5,030,457 | 7/1991 | Ng et al. . |
| 5,037,429 | 8/1991 | Hermes et al. . |
| 5,051,272 | 9/1991 | Hermes et al. . |
| 5,053,046 | 10/1991 | Janese . |
| 5,061,274 | 10/1991 | Kensey . |
| 5,096,959 | 3/1992 | Jones et al. . |
| 5,108,421 | 4/1992 | Fowler . |
| 5,112,652 | 5/1992 | Greene . |
| 5,118,783 | 6/1992 | Raju . |
| 5,129,882 | 7/1992 | Weldon et al. . |
| 5,192,300 | 3/1993 | Fowler . |
| 5,192,309 | 3/1993 | Stupka et al. . |
| 5,211,951 | 5/1993 | Sparer et al. . |
| 5,221,259 | 6/1993 | Weldon et al. . |
| 5,222,974 | 6/1993 | Kensey et al. . |
| 5,275,616 | 1/1994 | Fowler . |
| 5,282,827 | 2/1994 | Kensey et al. . |
| 5,292,332 | 3/1994 | Lee . |
| 5,302,628 | 4/1994 | Lim et al. ................................ 523/118 |
| 5,324,306 | 6/1994 | Makower et al. . |
| 5,330,446 | 7/1994 | Weldon et al. . |
| 5,370,660 | 12/1994 | Weinstein et al. . |
| 5,372,585 | 12/1994 | Tiefenbrun et al. . |
| 5,624,669 | 4/1997 | Leung et al. ......................... 424/78.35 |

OTHER PUBLICATIONS

T. Matsumoto, "Tissue Adhesives in Surgery," pp. 226–237.

P. Wittner, "Copolymerization in the Presence of Depolymerization Reactions", Multicomponent Polymer Systems, Chapter 10, Germany.

V. Percec et al., "A radical–anion mechanism for the phase transfer catalyzed depolymerization of poly(2,6–dimethyl–1,4–phenylene oxide)", Polymer Bulletin 24, 63–69 (1990).

Leonard, F. et al., *J. Applied Polymer Science*, vol. 10, pp. 259–272 (1966).

Leonard, F., *Annals New York Academy of Sciences*, vol. 146, pp. 203–213 (1968).

Tseng, Yin–Chao, et al., *J. Applied Biomaterials*, vol. 1, pp. 111–119 (1990).

Tseng, Yin–Chao, et al., *J. Biomedical Materials Research*, vol. 24, pp. 1355–1367 (1990).

"Controlled Release of Drugs: Polymers and Aggregate Systems," Morton Rosoff, Ed., VCH Publishers, Inc., 1989, New York, pp. 53–95.

PH-MODIFIED BIOCOMPATIBLE MONOMER AND POLYMER COMPOSITIONS

This is a Continuation of application Ser. No. 08/266,647 filed Jun. 28, 1994, now abandoned.

FIELD OF THE INVENTION

This invention relates to improved compositions useful as biomedical adhesives, sealants, implants and bioactive agent release matrices. This invention also relates to medical, surgical and other in vivo applications in which body tissue surfaces are joined or reinforced with biocompatible compositions.

BACKGROUND

The products in primary use for wound closure are surgical sutures and staples. Sutures are recognized to provide adequate wound support. However, sutures cause additional trauma to the wound site (by reason of the need for the needle and suture to pass through tissue) and are time-consuming to place, and, at skin level, can cause unattractive wound closure marks. Surgical staples have been developed to speed wound apposition. However, surgical staples also impose additional wound trauma and require the use of ancillary and often expensive devices for positioning and applying the staples.

To overcome these drawbacks, fast-acting surgical adhesives have been proposed. One group of such adhesives is the monomeric forms of alpha-cyanoacrylates.

Reference is made, for example, to U.S. Pat. No. 3,527,841 (Wicker et al.); U.S. Pat. No. 3,722,599 (Robertson et al.); U.S. Pat. No. 3,995,641 (Kronenthal et al.); and U.S. Pat. No. 3,940,362 (Overhults), which disclose that alpha-cyanoacrylates are useful as surgical adhesives. All of the foregoing references are hereby incorporated by reference herein.

Typically, when used as adhesives and sealants, cyanoacrylates are applied in monomeric form to the surfaces to be joined or sealed, where, typically, in situ anionic polymerization of the monomer occurs, giving rise to the desired adhesive bond or seal. Implants, such as rods, meshes, screws, and plates, may also be formed of cyanoacrylate polymers, formed typically by radical-initiated polymerization.

However, a drawback to the in vivo biomedical use of alpha-cyanoacrylate monomers and polymers has been their potential for causing adverse tissue response. For example, methyl alpha-cyanoacrylate has been reported to cause tissue inflammation at the site of application.

The adverse tissue response to alpha-cyanoacrylates appears to be caused by the products released during in vivo biodegradation of the polymerized alpha-cyanoacrylates. It is believed that formaldehyde is the biodegradation product most responsible for the adverse tissue response and, specifically, the high concentration of formaldehyde produced during rapid polymer biodegradation. Reference is made, for example, to F. Leonard et al., *Journal of Applied Polymer Science*, Vol. 10, pp. 259–272 (1966); F. Leonard, *Annals New York Academy of Sciences*, Vol. 146, pp. 203–213 (1968); Tseng, Yin-Chao, et al., *Journal of Applied Biomaterials*, Vol. 1, pp. 111–119 (1990), and to Tseng, Yin-Chao, et al., *Journal of Biomedical Materials Research*, Vol. 24, pp. 1355–1367 (1990).

For these reasons, cyanoacrylates have not come into widespread use for biomedical purposes.

Efforts to increase the tissue compatibility of alpha-cyanoacrylates have included modifying the alkyl ester group. For example, increasing the alkyl ester chain length to form the higher cyanoacrylate analogues, e.g., butyl-2-cyanoacrylates and octyl-2-cyanoacrylates, has been found to improve biocompatibility but the higher analogues biodegrade at slower rates than the lower alkyl cyanoacrylates.

Other examples of modified alpha-cyanoacrylates used in biomedical applications include carbalkoxyalkyl alpha-cyanoacrylates (see, for example, U.S. Pat. No. 3,995,641 to Kronenthal et al.), fluorocyanoacrylates (see, for example, U.S. Pat. No. 3,722,599 to Robertson et al.), and alkoxyalkyl 2-cyanoacrylates (see, for example, U.S. Pat. No. 3,559,652 to Banitt et al.). Other efforts have included mixing alpha-cyanoacrylates with dimethyl methylenemalonate and higher esters of 2-cyanoacrylic acid (see, for example, U.S. Pat. No. 3,591,676 to Hawkins et al.).

In other efforts to increase the usefulness of alpha-cyanoacrylate adhesive compositions for surgical applications, certain viscosity modifiers have been used in combination with alkyl alpha-cyanoacrylate monomers, such as methyl alpha-cyanoacrylate. See, for example, U.S. Pat. No. 3,564,078 (wherein the viscosity modifier is poly (ethyl 2-cyanoacrylate)) and U.S. Pat. No. 3,527,841 (wherein the viscosity modifier is poly(lactic acid)), both patents being to Wicker et al.

In a related application, U.S. Ser. No. 08/040,618, filed Mar. 31, 1993 (U.S. Pat. No. 5,328,687), the entire contents of which are hereby incorporated by reference, the use of formaldehyde scavengers has been proposed to improve biocompatibility of alpha-cyanoacrylate polymers, whose biodegradation produces formaldehyde, for use in in vivo applications. It is known that various compounds can affect polymerization of alpha-cyanoacrylate monomers, including acids to inhibit or slow polymerization (e.g., Leonard et al., U.S. Pat. No. 3,896,077), and bases to accelerate polymerization (e.g., Coover et al., U.S. Pat. No. 3,759,264 and Dombroski et al., U.S. Pat. No. 4,042,442).

SUMMARY OF THE INVENTION

It has not been known to regulate polymer biodegradation by regulating the pH of an immediate in vivo environment of a biocompatible composition. Such regulation would improve, for instance, the biocompatibility of 1,1-disubstituted ethylene polymers for in vivo applications, by controlling the rate of release of harmful byproducts (e.g., formaldehyde) and controlling the rate of degradation of the polymer in situ.

Combining the monomer composition with a biocompatible pH modifier effective to regulate the pH of an immediate environment of the in situ polymer will substantially improve the usefulness of polymers formed from such monomers, particularly in combination with use of formaldehyde scavengers.

The present invention is also directed to methods of using the above-described monomers, copolymers and polymers made therefrom for biomedical purposes.

The monomer compositions of this invention and polymers formed therefrom are useful as tissue adhesives, sealants for preventing bleeding or for covering open wounds, systems for delivery of therapeutic or other bioactive agents, and in other biomedical applications. They find uses in, for example, apposing surgically incised or traumatically lacerated tissues; setting fractured bone structures; retarding blood flow from wounds; aiding repair and regrowth of living tissue; and serving as matrices for delivering bioactive agents and as implants.

DETAILED DESCRIPTION OF PREFERRED EMBODIMENTS

Embodiments of the present invention provide a biocompatible monomer composition, comprising an effective amount of at least one biocompatible pH modifier effective to regulate the pH of an immediate in vivo environment of the polymer to a pH range at which the polymer's in vivo biodegradation proceeds at a different rate than it does at physiologic pH.

In a further embodiment, the present invention is directed to a biocompatible composition comprising a polymer whose in vivo biodegradation may produce formaldehyde, and a pH modifier as described previously, and optionally including a formaldehyde scavenger.

The monomers used in this invention are polymerizable, e.g. anionically polymerizable or free radical polymerizable, to form polymers which biodegrade. In some embodiments, they form active formaldehyde upon biodegradation.

Monomer compositions of this invention may be applied to a surface to be sealed or joined together with a second surface in vivo, where, typically, in situ anionic polymerization of the monomer occurs, giving rise to the desired adhesive bond or seal.

Useful 1,1-disubstituted ethylene monomers include, but are not limited to, monomers of the formula:

$$CHR=CXY \quad (I)$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (I) include alpha-cyanoacrylates, vinylidene cyanides, C$_1$–C$_4$ alkyl homologues of vinylidene cyanides, dialkyl 2-methylene malonates, acylacrylonitriles, vinyl sulfinates and vinyl sulfonates of the formula CH$_2$=CX'Y' wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are alpha-cyanoacrylates. These monomers are known in the art and have the formula

(II)

wherein R$^2$ is hydrogen and R$^3$ is a hydrocarbyl or substituted hydrocarbyl group; a group having the formula —R$^4$—O—R$^5$—O—R$^6$, wherein R$^4$ is a 1,2-alkylene group having 2–4 carbon atoms, R$^5$ is an alkylene group having 2–4 carbon atoms, and R$^6$ is an alkyl group having 1–6 carbon atoms; or a group having the formula

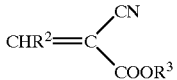

wherein R$^7$ is —CH$_2$—,

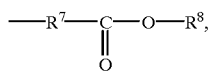

or —C(CH$_3$)$_2$—, and R$^8$ is an organic radical.

Examples of suitable hydrocarbyl and substituted hydrocarbyl groups include straight chain or branched chain alkyl groups having 1–16 carbon atoms; straight chain or branched chain C$_1$–C$_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

In the cyanoacrylate monomer of formula (II), R$^3$ is preferably an alkyl group having 1–10 carbon atoms or a group having the formula —AOR$^9$, wherein A is a divalent straight or branched chain alkylene or oxyalkylene radical having 2–8 carbon atoms, and R$^9$ is a straight or branched alkyl radical having 1–8 carbon atoms.

Examples of groups represented by the formula —AOR$^9$ include 1-methoxy-2-propyl, 2-butoxyethyl, 2-isopropoxyethyl, 2-methoxyethyl, 2-ethoxyethyl and 3-methoxybutyl.

Especially advantageous alpha-cyanoacrylate monomers for use in this invention are methyl alpha-cyanoacrylate, butyl alpha-cyanoacrylate, 2-octyl alpha-cyanoacrylate, 1-methoxy-2-propyl cyanoacrylate, 2-butoxyethyl cyanoacrylate, 2-isopropoxyethyl cyanoacrylate and 3-methoxybutyl cyanoacrylate. Equally advantageous are 2-methylene malonates, such as dimethyl 2-methylenemalonate.

The alpha-cyanoacrylates of formula (II) wherein R$^3$ is a hydrocarbyl or substituted hydrocarbyl group can be prepared according to methods known in the art. Reference is made, for example, to U.S. Pat. Nos. 2,721,858 and 3,254,111, each of which is hereby incorporated by reference herein. For example, the alpha-cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (II) wherein R$^3$ is a group having the formula —R$^4$—O—R$^5$—O—R$^6$ can be prepared according to the method disclosed in U.S. Pat. No. 4,364,876 (Kimura et al.), which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or paraformaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The alpha-cyanoacrylates of formula (II) wherein R$^3$ is a group having the formula

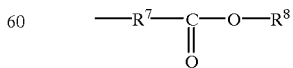

can be prepared according to the procedure described in U.S. Pat. No. 3,995,641 (Kronenthal et al.), which is hereby incorporated by reference. In the Kronenthal et al. method, such alpha-cyanoacrylate monomers are prepared by reacting an alkyl ester of an alpha-cyanoacrylic acid with a cyclic 1,3-diene to form a Diels-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Examples of monomers of formula (II) include cyanopentadienoates and alpha-cyanoacrylates of the formula:

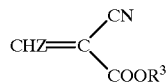

(III)

wherein Z is —CH=CH$_2$ and R$^3$ is as defined above. The monomers of formula (III) wherein R$^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is incorporated by reference herein.

Compositions of this invention comprise an effective amount of a biocompatible pH modifier to regulate the pH of an immediate in situ environment of the polymer to a pH level at which the polymer's in vivo biodegradation proceeds at a different rate than it does at a physiologic pH ("effective amount"). An effective amount of a pH modifier effective to achieve the desired in situ pH modification will depend on the acidity or basicity (pKa or pKb) of the compound used, the pH of the polymer composition used when in situ, the in vivo environment's physiologic pH, and the release rate of biodegradation products resulting from the pH-modified biodegradation rate. An effective amount of pH modifier may be selected with regard to any formaldehyde scavenger or other component added to control levels of biodegradation products released. As well, a non-toxic pH modifier (e.g., an acid) is preferably used, or the pH modifier is used in an effective amount that minimizes any potential toxic effect.

For instance, in embodiments of the invention, a non-encapsulated, acidic pH modifier may be present in an effective amount greater than 1% by weight of the composition. In microencapsulated forms, the amount of pH modifier added may be varied from a minimum effective amount up to a maximum loading permitted by the microcapsule and any toxicity limit, according to the particular monomer or polymer composition and application. At the same time, the pH modifier should not significantly affect (inhibit or accelerate) in vivo polymerization of the monomer composition or otherwise interfere with the composition's efficacy for medical or surgical applications.

An acidic or basic pH modifying compound, and its concentration in the composition, may be selected according to the in vivo pH range to be achieved in an immediate environment of the in situ polymerized or crosslinked adhesive composition. The desired in situ pH level depends on the particular monomer or polymer used and on whether that polymer's in vivo biodegradation rate is desired to be slower or faster than its biodegradation rate at the physiologic pH of the particular in vivo application. One skilled in the biocompatible monomer and polymer field will be able, upon reading this disclosure and with some routine experimentation, to select the pH modifier best suited for a given polymer or monomer composition and the particular application for which it is used.

The pH modifier may be selected to modify, in vivo, the pH of an immediate in situ environment of the polymer to a pH level at which in vivo biodegradation of the in situ polymer (and low molecular weight materials in the composition) proceeds more slowly than it does at a physiologic pH. This results in retarding the rate of release of formaldehyde and other degradation products, thereby reducing their toxic effects since, e.g., formaldehyde can be more completely eliminated before substantial, toxic concentrations occur in situ.

In such embodiments, the pH modifier may include, for example, but is not limited to, an acidic compound or anhydrous precursor thereof or a chemically protected acid. For example, the pH modifier may comprise at least one member selected from the group consisting of: amino acids; carboxylic acids and salts thereof; di-acids and salts thereof; poly-acids and salts thereof; esters that are easily hydrolyzable in vivo; lactones that are easily hydrolyzable in vivo; organic carbonates; enolic compounds; acidic phenols; polyphenolic compounds; aromatic alcohols; ammonium compounds or salts thereof; boron-containing compounds; sulfonic acids and salts thereof; sulfinic acids and salts thereof; phosphorus-containing compounds; acid halides; chloroformates; acid gases; acid anhydrides; inorganic acids and salts thereof; and polymers having functional groups of at least one of the preceding members. The pH modifier of this invention may, for example, comprise at least one member selected from the group consisting of: glycine; alanine; proline; lysine; glutaric acid; D-galacturonic acid; succinic acid; lactic acid; glycolic acid; poly(acrylic acid); sodium acetate; diglycolic anhydride; succinic anhydride; citraconic anhydride; maleic anhydride; lactide; diethyl oxalate; Meldrum's acid; diethyl carbonate; dipropyl carbonate; diethyl pyrocarbonate; diallyl pyrocarbonate; di-tert-butyl dicarbonate; ascorbic acid; catechin; ammonium chloride; D-glucosamine hydrochloride; 4-hydroxyephedrine hydrochloride; boric acid; nitric acid; hydrochloric acid; sulfuric acid; ethanesulfonic acid; and p-toluenesulfonic acid; 2-aminoethylphosphoric acid; methylphosphonic acid; dimethylphosphinic acid; methyl chloroformate; sulfur dioxide; and carbon dioxide. Glutaric acid and diethyl carbonate are particularly preferred in embodiments of the invention.

The pH modifier may alternatively be selected to modify, in vivo, a pH of an immediate in vivo environment of the polymer to a pH level at which in vivo biodegradation of the in situ polymer proceeds more quickly than it does at a physiologic pH. Basic pH modifiers allow the use of polymer materials otherwise degrading slowly or not at all in vivo, e.g., butyl alpha-cyanoacrylate or 2-octyl alpha-cyanoacrylate. The pH modifier is added in an amount sufficient to accelerate the polymer's biodegradation, but the accelerated release of biodegradation products (e.g., formaldehyde) must remain within physiologically tolerable ranges. In this aspect, a formaldehyde scavenger may also be added to keep formaldehyde levels within tolerable levels, for instance, in the manner of related application, U.S. Ser. No. 08/040,618.

In such embodiments, the pH modifier may include a basic compound or anhydrous precursor thereof, and/or a chemically protected base. For example, the pH modifier may comprise at least one member selected from the group consisting of: hydroxides; alkoxides; basic carbonates; nitrogen-containing compounds; amines; alkaloids; hydrides; organolithium compounds; Grignard reagents; carbanions; and polymers having functional groups of at least one of the preceding members. The pH modifier (whether single or in combination) may be, for example, selected from the group consisting of: sodium hydroxide; potassium hydroxide; sodium methoxide; potassium t-butoxide; sodium carbonate; calcium carbonate; dibutylamine; tryptamine; sodium hydride; calcium hydride; butyllithium; and ethylmagnesium bromide.

The present invention encompasses situations in which formaldehyde is released as a byproduct of in situ biodegradation of the biocompatible polymer. A formaldehyde concentration-reducing agent or formaldehyde scavenger, e.g., sodium bisulfite, may be added to the compositions and methods of this invention to control formaldehyde release in situ and to minimize harmful effects therefrom, as disclosed in related application, U.S. Ser. No. 08/040,618, incorporated herein by reference. However, an acid pH modifier-containing composition herein disclosed can further minimize active formaldehyde concentrations in situ in the following manner. The pH modifier regulates the immediate pH environment of the in situ polymerized composition such that the polymer's in situ biodegradation is slowed, thereby keeping in situ formaldehyde concentrations at a level that can be handled physiologically and that will not, in an initial burst, overwhelm any formaldehyde scavenger that is present.

The pH modifier used in this invention may either be in free form or in a protected form. For instance, it may be in a form that is insoluble in the monomer of a monomer composition, such as a free acid or a microencapsulated form, or may be in a chemically protected form that may be soluble or insoluble in such monomer compositions. Once in vivo, the pH modifier may diffuse through the microcapsule or be released by bioerosion of the microcapsule, into the in situ polymer. The microcapsule may be formulated so that the pH modifier is released from the microcapsule continuously over a period of time during the biodegradation of the in situ polymer. Alternatively, the microencapsulated pH modifier may be formed to release rapidly and transiently, after a time delay, or even intermittently, vis-à-vis the life of the in situ polymer, depending on when the pH modifier is desired to have effect. For example, delayed release of a basic pH modifier may be desired to cause the polymer to begin to degrade rapidly after it has served a significant portion of its useful life. As well, pH modifiers may be used in combination, allowing, e.g., quick release of an acidic pH modifier followed by later release of a basic pH modifier, for more refined control of the polymer's biodegradation.

For purposes of this invention, the microencapsulated form of the pH modifier is advantageous because this embodiment prevents or substantially reduces preapplication effects of the pH modifier, e.g., a basic pH modifier, thereby increasing shelf-life and facilitating handling of the monomer composition during use.

Microencapsulation of the pH modifier can be achieved by many known microencapsulation techniques. For example, microencapsulation can be carried out by dissolving a coating polymer in a volatile solvent, e.g., methylene chloride, to a polymer concentration of about 6% by weight; adding a pH modifying compound (selected to be acidic or basic according to the pH level to be achieved in situ) in particulate form to the coating polymer/solvent solution under agitation, to yield a pH modifier concentration of 2% to 10% by weight; adding the resulting polymer dispersion to a methylene chloride solution containing a phase inducer, such as silicone oil, under agitation; allowing the mixture to equilibrate for about 20 minutes; further adding the mixture slowly to a non-solvent, such as heptane, under rapid agitation; allowing the more volatile solvent to evaporate under agitation; removing the agitator; separating the solids from the silicone oil and heptane; and washing and drying the microparticles. The size of the microparticles will range from about 0.001 to about 1000 microns.

The microencapsulating coating polymer should be able to undergo in vivo bioerosion or to permit diffusion of the pH modifier, and should have low inherent moisture content. Bioerosion preferably occurs at rates greater than or similar to the rate of degradation of the base polymer. Such "bioerosion" can occur as a result of the physical or chemical breakdown of the encapsulating material, for example, by the encapsulating material passing from solid to solute in the presence of body fluids, or by biodegradation of the encapsulating material by agents present in the body.

Examples of coating materials that can be used to microencapsulate the pH modifier include, but are not limited to: polyesters, such as polyglycolic acid, polylactic acid, copolymers of polyglycolic acid and polylactic acid, polycaprolactone, poly-β-hydroxybutyrate, copolymers of ε-caprolactone and δ-valerolactone, copolymers of ε-caprolactone and DL-dilactide, and polyester hydrogels; polyvinylpyrrolidone; polyamides; gelatin; albumin; proteins; collagen; poly(orthoesters); poly(anhydrides); poly(alkyl-2-cyanoacrylates); poly(dihydropyrans); poly(acetals); poly(phosphazenes); poly(urethanes); poly(dioxinones); cellulose; and starches.

Examples of a phase inducer that can be added include silicone oil, mineral oil, polyethylene, polyisobutylene, and polybutadiene.

Compositions of this invention may further contain a stabilizer and/or one or more adjuvant substances, such as thickening agents, plasticizers, or the like, to improve its medical utility for particular medical applications.

Examples of suitable stabilizers include sulfur dioxide, sulfonic acid, lactone, boron trifluoride, hydroquinone, hydroquinone monomethyl ether, catechol, pyrogallol, benzoquinone, 2-hydroxybenzoquinone, p-methoxy phenol, t-butyl catechol, organic acid, butylated hydroxy anisole, butylated hydroxy toluene, t-butyl hydroquinone, alkyl sulfate, alkyl sulfite, 3-sulfolene, alkylsulfone, alkyl sulfoxide, mercaptan, and alkyl sulfide.

Suitable thickeners include, for example, polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene.

Examples of suitable plasticizers include dioctyl phthalate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, dibutyl phthalate, trioctyl trimellitate, and dioctyl glutarate.

To improve the cohesive strength of adhesives formed from the compositions of this invention, difunctional monomeric cross-linking agents may be added to compositions or used in methods of this invention in vivo or ex vivo. Such crosslinking agents are known. Reference is made, for example, to U.S. Pat. No. 3,940,362 (Overhults), which is hereby incorporated by reference herein. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). When used ex vivo, a catalytic amount of a free radical initiator is added to initiate polymerization of the cyanoacrylate monomer/crosslinking agent blend. Such compositions can be molded or otherwise formed to provide preformed implants and prosthetic devices for surgical use, such as rods, meshes, plates, screws, and fasteners.

The compositions of this invention may further contain fibrous reinforcement and colorants, e.g., dyes and pigments. Examples of suitable fibrous reinforcement include PGA microfibrils, collagen microfibrils, cellulosic microfibrils, and olefinic microfibrils. Examples of suitable colorants include 1-hydroxy-4-[4-methylphenylamino]-9,10 anthracenedione (FD&C violet No. 2); disodium salt of 6-hydroxy-5-[(4-sulfophenyl)axo]-2-naphthalene-sulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); 2-(1,3-dihydro-3-oxo-5-sulfo-2H-indol-2-ylidene)-2,3-dihydro-3-oxo-1H-indole-5-sulfonic acid disodium salt (FD&C Blue No. 2); and [phthalocyaninato (2-)] copper.

The biocompatible adhesive compositions of this invention can be used, for example, to join together two surfaces, at least one of the surfaces being body or living tissue, by applying the composition to at least one of the surfaces. Depending on the particular requirements of the user, the compositions of this invention can be applied by known means, such as with a glass stirring rod, sterile brush, medicine dropper, spray bottle or other non-aerosol means. However, in many situations, a pressurized aerosol dispensing package is advantageous, in which the adhesive composition is in solution with a compatible anhydrous or other aerosol propellant. Aerosol application of the monomers is particularly advantageous for use in hemostasis. The compositions of this invention may also be stored in and dispensed from a two-phase container, in which the pH modifier is kept apart from the monomer composition until shortly before or at the moment of applying the adhesive composition in situ to the in vivo surfaces to be bonded. If a formaldehyde concentration-reducing agent is also present, it may be present in either of the above two phases, or in a separate third phase of a multi-phase container.

In one embodiment, the present invention is directed to a method of joining together in vivo two surfaces, one or both of which may be a body tissue, which comprises (a) applying to at least one of said surfaces a biocompatible composition of this invention, and (b) maintaining the surfaces in contact until said composition joins together the two surfaces (e.g., by polymerization of the monomer composition). One of said surfaces can be body tissue and the other surface a prosthetic device or the like, or both surfaces may be body tissue. As one example of a composition which may be used to practice this method, said composition may comprise: (1) at least one monomer (e.g., a monomer of formula (I)) which forms a polymer whose in vivo biodegradation proceeds at a physiologic pH (and may release formaldehyde); and (2) an effective amount of a biocompatible pH modifier to regulate the pH of an immediate in situ environment of the biocompatible polymer to a pH level at which said polymer biodegrades at a different rate than it does at said physiologic pH. The pH modifier may be selected to slow or to accelerate the polymer's biodegradation.

Various methods for repairing or strengthening damaged living tissue to prevent the escape of fluids therethrough exist which may employ a composition of the invention. For example, a method for repairing or dressing living tissue may comprise: (a) applying to the tissue a surgical sealant comprising the biocompatible composition including a pH modifier of this invention; and (b) allowing the composition to polymerize. A method for stemming the flow of blood from small vessels may comprise applying to said vessels a surgical sealant or hemostatic agent comprising a biocompatible monomer composition including a pH modifier. A method of dressing burns to promote the healing thereof may comprise (a) covering said burn with a biocompatible composition of this invention; and (b) allowing the composition to polymerize in situ; and methods of dressing wounds to promote the healing thereof may comprise (a) covering said wound with a biocompatible composition of this invention; and (b) allowing the composition to polymerize.

Repairing injured tissues (for example, to control bleeding) may comprise, for example, sponging to remove superficial body fluids and subsequent application to the exposed tissue of a composition of the invention. For example, a monomer composition polymerizes to a thin film of polymer while in contact with the tissue surface. For bonding separate surfaces of body tissues, the monomer is applied to at least one surface, and the surfaces are brought quickly together while the monomer polymerizes in contact with both surfaces.

In another embodiment, the present invention may be used in a method for effecting in vivo administration of a bioactive agent, comprising introducing into a body a composition of this invention, which may comprise: (a) a polymer whose in vivo biodegradation may or may not release formaldehyde; (b) an effective amount of a biocompatible pH modifier; and (c) a bioactive amount of a bioactive agent, wherein biodegradation of the polymer or diffusion of the bioactive agent effects its in vivo release. The bioactive agent may be encapsulated in a suitable biodegradable material for controlling release of the bioactive agent. The polymer may be one degrading slowly or not at all or may be hydrolytically sensitive, at an in vivo physiologic pH. In the former case, a basic pH modifier may be added to promote biodegradation of the polymer. The composition may also include an effective amount of at least one biocompatible agent effective to reduce active formaldehyde concentration levels, e.g., a formaldehyde scavenger.

The compositions may be used further to administer therapeutic agents into the body. The composition will form a matrix for the therapeutic agent, with the therapeutic agent being released in vivo from the matrix by diffusion or by biodegradation, over time, of the polymer. For example, a composition comprising the monomer (or polymer form of the monomer, since in this application, polymerization need not occur in situ), a biocompatible pH modifier of this invention, an optional biocompatible formaldehyde scavenger, and a therapeutic agent are introduced into the body where the polymer undergoes biodegradation, gradually releasing the therapeutic agent. Alternatively, the therapeutic agent may diffuse out from the composition, into the body, before polymeric biodegradation ends or even begins.

The monomers are readily polymerized to addition-type polymers and copolymers.

In most bonding applications using compositions of this invention, polymerization of the monomers is catalyzed by small amounts of moisture on the surface of the adherents. Therefore, desired bonding of tissues and hemostasis proceed well in the presence of blood and other body fluids. The bonds formed are of adequate flexibility and strength to withstand normal movement of tissue. In addition, bond strength is maintained as natural tissue healing proceeds concurrently with polymer assimilation.

Compositions employed in the invention are sterilizable by conventional methods such as by autoclave or by aseptic filtration techniques.

The invention is further illustrated by the following non-limiting examples.

EXAMPLES

In the Examples below, the following terms are defined as follows:
IPECA—2-isopropoxyethyl cyanoacrylate
DMM—dimethyl 2-methylenemalonate
3MBCA—3-methoxybutyl cyanoacrylate
2OCA—2-octyl cyanoacrylate
monomer(s)—refers generically to IPECA, DMM, 3MBCA and/or 2OCA

Examples 1–18 and Control Examples 1C–18C

Examples 1–18 and Control Examples 1C–18C illustrate the effect of a biocompatible pH modifier on the biodegradation of a 1,1-disubstituted ethylene monomer polymerized in situ. The compositions of Examples 1–18 each contain a pH modifier (in free or microencapsulated form) while the compositions of Control Examples 1C–18C contain sodium chloride (NaCl), polycaprolactone microcapsules, or no additive.

The formulations of the compositions prepared in Examples 1–18 and Control Examples 1C–18C are shown in Tables IA and IB, respectively.

The compositions of the examples are prepared as follows. Appropriate weight ratios of the monomer and an additive are mixed thoroughly by shaking. (Solid pH modifiers and sodium chloride are ground or milled to a fine particle size before mixing.) The resulting mixture is quickly poured onto a glass plate equipped with a 4 cm×8 cm boundary. The glass plate is pre-treated with chlorotrimethylsilane and the boundary is fabricated with caulking cord material. The mixture is spread evenly to all edges. Polymerization of the monomer mixture is then accelerated by spraying with a 1% aqueous sodium bicarbonate solution (Examples 1–3, 5, 9–18, 1C–3C, 5C, and 9C–18C) or a 1:2:97 triethylamine/methanol/heptane mixture (Examples 4, 6–8, 4C, and 6C–8C). The hardened polymer film is gently scraped off the glass plate, cut away from the boundary and dried. It is further cut into two halves, each of 2 cm×8 cm, for duplicate runs.

In Examples 13–15, the additive is sprinkled evenly on the glass plate and the monomer is then carefully added, instead of the two being mixed directly.

In vitro biodegradation (simulating in vivo biodegradation) of each 2 cm×8 cm polymer film is then carried out as follows. The polymer film, encaged in aluminum mesh, is placed in a pH 7.4 buffer (e.g., monobasic potassium phosphate and dipotassium phosphate). Biodegradation is carried out at 37±2° C. for 168 hours (Examples 1–9, 13–18, 1C–9C, and 13C–18C) or at 37±2° C. for 192 hours (Examples 10–12, and 10C–12C). The partially degraded film is separated from the buffer solution and dried. The buffer solution is subjected to formaldehyde determination.

Determination of the amount of formaldehyde generated during biodegradation of the polymer films may be accomplished as disclosed in related application U.S. Ser. No. 08/040,618 (U.S. Pat. No. 5,328,687).

In the following tables, the term "μg formaldehyde detected per g polymer" means the amount of formaldehyde generated in micrograms divided by the original polymer weight in grams (excluding the weight of the pH modifier or control additive).

TABLE IA

Examples 1–18

| Example No. | Monomer | Additive | Additive Weight % | μg Formaldehyde Detected per g Polymer | % Change of Formaldehyde Detected |
| --- | --- | --- | --- | --- | --- |
| 1 | IPECA | diethyl carbonate | 2.5 | 1652 | −77.4 |
| 2 | IPECA | diethyl carbonate | 5.0 | 1278 | −87.0 |
| 3 | IPECA | diethyl carbonate | 7.5 | 8806 | −14.4 |
| 4 | IPECA | lactide | 7.0 | 1161 | −73.3 |
| 5 | IPECA | glucosamine hydrochloride | 9.0 | 6082 | −19.9 |
| 6 | IPECA | ascorbic acid | 2.0 | 5226 | −66.7 |
| 7 | IPECA | glutaric acid | 1.0 | 13,788 | −7.3 |
| 8 | IPECA | glutaric acid/ polycaprolactone microcapsules | 8.0 | 3023 | −20.0 |
| 9 | 3MBCA | glycine | 8.0 | 1909 | −8.7 |
| 10 | DMM | diethyl oxalate | 6.0 | 1723 | −61.4 |
| 11 | DMM | tryptamine | 3.0 | 2538 | +22.6 |
| 12 | DMM | potassium carbonate | 2.0 | 2372 | +16.2 |
| 13 | IPECA | tryptamine/polycaprolactone microcapsules | 4.0 | 10,376 | +53.4 |
| 14 | IPECA | tryptamine/polycaprolactone microcapsules | 6.0 | 9961 | +63.7 |
| 15 | IPECA | tryptamine/polycaprolactone microcapsules | 8.0 | 9094 | +46.9 |

TABLE IA-continued

Examples 1–18

| Example No. | Monomer | Additive | Additive Weight % | μg Formaldehyde Detected per g Polymer | % Change of Formaldehyde Detected |
|---|---|---|---|---|---|
| 16 | IPECA | sodium carbonate/poly-caprolactone microcapsules | 10.0 | 6949 | +63.6 |
| 17 | 3MBCA | sodium methoxide | 5.0 | 4389 | +856.2 |
| 18 | 20CA | sodium hydroxide | 8.5 | 2351 | +1379.0 |

TABLE IB

Control Examples 1C–18C

| Example No. | Monomer | Additive | Additive Weight % | μg Formaldehyde Detected per g Polymer | % Change of Formaldehyde Detected |
|---|---|---|---|---|---|
| 1C | IPECA | sodium chloride | 2.5 | 7295 | 0 |
| 2C | IPECA | sodium chloride | 5.0 | 9856 | 0 |
| 3C | IPECA | sodium chloride | 7.5 | 10,293 | 0 |
| 4C | IPECA | sodium chlaride | 7.0 | 4355 | 0 |
| 5C | IPECA | sodium chloride | 9.0 | 7595 | 0 |
| 6C | IPECA | sodium chloride | 2.0 | 5,698 | 0 |
| 7C | IPECA | sodium chloride | 1.0 | 14,880 | 0 |
| 8C | IPECA | sodium chloride | 8.0 | 3780 | 0 |
| 9C | 3MBCA | sodium chloride | 8.0 | 2091 | 0 |
| 10C | DMM | sodium chloride | 6.0 | 4466 | 0 |
| 11C | DMM | sodium chloride | 3.0 | 2070 | 0 |
| 12C | DMM | sodium chloride | 2.0 | 2041 | 0 |
| 13C | IPECA | polycaprolactone microcapsules | 4.0 | 6764 | 0 |
| 14C | IPECA | polycaprolactone microcapsules | 6.0 | 6085 | 0 |
| 15C | IPECA | polycaprolactone microcapsules | 8.0 | 6189 | 0 |
| 16C | IPECA | polycaprolactone microcapsules | 10.0 | 4248 | 0 |
| 17C | 3MBCA | none | 0 | 459 | 0 |
| 18C | 20CA | none | 0 | 159 | 0 |

The monomer IPECA is polymerized by azoisobutyronitrile (AIBN) at 70° C. to give a polymer of approximately 25,000 molecular weight. In the following Examples, polymer(s) refers generically to the IPECA polymer prepared in this manner.

Examples 19–20 and Control Examples 19C–20C

Examples 19–20 and Control Examples 19C–20C illustrate the effect of a biocompatible pH modifier on the biodegradation of a 1,1-disubstituted ethylene polymer. The compositions of Examples 19–20 each contain a pH modifier while the compositions of Control Examples 19C–20C contain sodium chloride (NaCl).

The formulations of the compositions prepared in Examples 19–20 and Control Examples 19C–20C are shown in Table II.

The compositions of the examples are prepared as follows. The polymer is dissolved in methylene chloride to give a polymer concentration of about 15%. The resulting polymer solution and an additive (either a pH modifier or sodium chloride) are mixed thoroughly in the appropriate weight ratio by shaking. (Solid pH modifiers and sodium chloride are ground or milled to a fine particle size before mixing.) The resulting mixture is quickly poured onto a glass plate equipped with a 4 cm×8 cm boundary. The glass plate is pre-treated with chlorotrimethylsilane and the boundary is fabricated with caulking cord material. The inside border is painted with melted paraffin wax. The mixture is spread evenly to all edges. Following evaporation of solvent, the polymer film is gently scraped off the glass plate, cut away from the boundary and dried. It is further cut into two halves, each of 2 cm×8 cm, for duplicate runs.

In vitro biodegradation (simulating in vivo biodegradation) of the polymer films and formaldehyde determination are carried out using the same procedures followed in Examples 1–9 and 13–18 and Control Examples 1C–9C and 13C–18C. The results of Examples 19–20 and Control Examples 19C–20C are shown in Table II.

TABLE II

Examples 19–20 and Control Examples 19C–20C

| Example No. | Polymer | Additive | Additive Weight % | μg Formaldehyde Detected per g Polymer | % Change of Formaldehyde Detected |
|---|---|---|---|---|---|
| 19 | IPECA | hydrochloric acid | 1.0 | 329 | −37.0 |
| 20 | IPECA | methylphosphonic acid | 5.0 | 906 | −55.1 |
| 19C | IPECA | sodium chloride | 1.0 | 522 | 0 |
| 20C | IPECA | sodium chloride | 5.0 | 2018 | 0 |

We claim:

1. A method comprising:
   (a) applying to an in vivo surface a biocompatible composition comprising:
      (1) at least one monomer which forms a polymer in situ at a physiologic pH;
      (2) an effective amount of at least one biocompatible pH modifier to modify the pH of an immediate in vivo environment of said polymer to a pH range at which said polymer biodegrades at a different rate than it does at physiologic pH, without said pH modifier significantly affecting the monomer's polymerization in situ, said at least one biocompatible pH modifier being thoroughly mixed with said at least one monomer and wherein said pH modifier is insoluble in the monomer, or in a microcapsule or chemically protected form; and
      (3) at least one thickening agent different from said pH modifier; and
   (b) allowing the monomer composition to polymerize in situ.

2. The method of claim 1, wherein said thickening agent is at least one member selected from the group consisting of polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylate and butadiene.

3. A method comprising:
   (a) applying to an in vivo surface a biocompatible composition comprising:
      (1) at least one monomer which forms a polymer in situ at a physiologic pH; and
      (2) an effective amount of at least two different biocompatible pH modifiers having different release rates to modify the pH of an immediate in vivo environment of said polymer to a pH range at which said polymer biodegrades at a different rate than it does at physiologic pH, without said pH modifiers significantly affecting the monomer's polymerization in situ, said at least two biocompatible pH modifiers being thoroughly mixed with said at least one monomer and said pH modifiers being insoluble in the monomer, or in a microcapsule or chemically protected form; and
   (b) allowing the monomer composition to polymerize in situ.

4. A biocompatible monomer composition, comprising:
   (a) at least one monomer comprised of a 1,1-disubstituted ethylene monomer, which forms a polymer in vivo at a physiologic pH; and
   (b) an effective amount of a biocompatible pH modifier to regulate, after in vivo polymerization of the monomer in situ, the pH of an immediate in vivo environment of the polymer to a pH range at which the polymer biodegrades in vivo at a different rate than it does at physiologic pH, without significantly affecting in situ polymerization of the monomer,
   wherein said pH modifier is in at least one form selected from the group consisting of:
      (a) insoluble in the monomer,
      (b) in a microcapsule,
      (c) chemically protected and insoluble in the monomer,
      (d) chemically protected and basic,
      (e) acidic and chemically protected form of at least one member selected from the group consisting of amino acids; di-acids and salts thereof; polyacids and salts thereof; esters that are easily hydrolyzable in vivo; lactones that are easily hydrolyzable in vivo; organic carbonates; enolic compounds; acidic phenols; polyphenolic compounds; aromatic alcohols; boron-containing compounds; sulfonic acids and salts thereof; sulfinic acids and salts thereof; phosphorus-containing compounds; acid halides; chloroformates; acid gases; acid anhydrides; inorganic acids and salts thereof; and polymers having functional groups of at least one member selected from the group consisting of amino acids, di-acids and salts thereof, polyacids and salts thereof, lactones that are easily hydrolyzable in vivo, organic carbonates, enolic compounds, acidic phenols, polyphenolic compounds, aromatic alcohols, boron-containing compounds, sulfonic acids and salts thereof, sulfinic acids and salts thereof, phosphorus-containing compounds, acid halides, chloroformates, acid gases, acid anhydrides, and inorganic acids and salts thereof, and
      (f) acidic and chemically protected form of at least one member selected from the group consisting of D-galacturonic acid; succinic acid and succinic anhydride; glycolic acid; poly(acrylic acid); acetic acid; diglycolic ahyhdride; citraconic anhydride; maleic anhydride; diethyl oxalate; Meldrum's acid; diethyl carbonate; dipropyl carbonate; diethyl pyrocarbonate; diallyl pyrocarbonate; di-tert-butyl dicarbonate; ascorbic acid; catechin; D-glucosamine hydrochloride; 4-hydroxy-ephedrin hydrochloride; boric acid; nitric acid; hydrochloric acid; sulfuric acid; ethanesulfonic acid; p-toluenesulfonic acid; 2-aminoethylphosphoric acid; methylphosphonic acid; dimethylphosphinic acid; methyl chloroformate; sulfur dioxide; carbon dioxide; and combinations of the above materials.

5. The composition of claim 4, wherein the polymer biodegrades in vivo at physiologic pH.

6. The composition of claim 4, wherein the pH modifier is in a form that is substantially insoluble in the monomer.

7. The composition of claim 4, wherein the pH modifier is microencapsulated in a coating polymer that has a low inherent moisture content and that undergoes in vivo bioerosion.

8. The composition of claim 7, wherein the pH modifier is capable, in vivo, of diffusing through the coating polymer.

9. The composition of claim 4, wherein the pH modifier is effective to promote a faster in vivo biodegradation of the polymer than that occurring at physiologic pH.

10. The composition of claim 4, wherein the pH modifier is effective to promote a slower in vivo biodegradation of the polymer than that occurring at physiologic pH.

11. The composition of claim 4, wherein said pH modifier is a non-encapsulated acidic pH modifier and comprises at least about 1% by weight of the composition.

12. The composition of claim 4, wherein the at least one monomer is an alpha-cyanoacrylate or a 2-methylene malonate.

13. The composition of claim 11, wherein the alpha-cyanoacrylate is methyl cyanoacrylate, butyl cyanoacrylate, 2-octyl cyanoacrylate, 1-methoxy-2-propyl cyanoacrylate, 2-butoxyethyl cyanoacrylate, or 2-isopropoxyethyl cyanoacrylate or 3-methoxybutyl cyanoacrylate.

14. The composition of claim 4, further comprising an effective amount of at least one biocompatible agent to reduce active formaldehyde concentration levels.

15. The composition of claim 4, wherein the pH modifier is a chemically protected acid.

16. The composition of claim 4, wherein the pH modifier is in chemically protected acidic form.

17. The composition of claim 4, wherein the pH modifier comprises at least one member selected from the group consisting of: glycine; alanine; proline; lysine; glutaric acid; D-galacturonic acid; succinic acid; lactic acid; glycolic acid; poly(acrylic acid); sodium acetate; diglycolic anhydride; succinic anhydride; citraconic anhydride; maleic anhydride; lactide; diethyl oxalate; Meldrum's acid; diethyl carbonate; dipropyl carbonate; diethyl pyrocarbonate; diallyl pyrocarbonate; di-tert-butyl dicarbonate; ascorbic acid; catechin; ammonium chloride; D-glucosamine hydrochloride; 4-hydroxyephedrine hydrochloride; boric acid; nitric acid; hydrochloric acid; sulfuric acid; ethanesulfonic acid; p-toluenesulfonic acid; 2-aminoethylphosphoric acid; methylphosphonic acid; dimethylphosphinic acid; and methyl chloroformate.

18. The composition of claim 4, wherein the pH modifier is a chemically protected base or a base or anhydrous precursor thereof.

19. The composition of claim 4, wherein the pH modifier comprises at least one member selected from the group consisting of:

hydroxides;
alkoxides;
basic carbonates;
nitrogen-containing compounds;
amines;
alkaloids;
hydrides;
organolithium compounds;
Grignard reagents;
carbanions; and
polymers having functional groups of at least one of the preceding members.

20. The composition of claim 4, wherein the pH modifier comprises at least one member selected from the group consisting of: sodium hydroxide; potassium hydroxide; sodium methoxide; potassium t-butoxide; sodium carbonate; dibutylamine; tryptamine; sodium hydride; calcium hydride; butyllithium; and ethylmagnesium bromide.

21. The composition of claim 4, wherein the polymer biodegrades slowly or not at all at physiologic pH.

22. The composition of claim 21, wherein the polymer comprises at least one member selected from the group consisting of butyl alpha-cyanoacrylate and octyl alpha-cyanoacrylate.

23. The composition of claim 21, further comprising an effective amount of at least one biocompatible agent to reduce active formaldehyde concentration levels.

24. A surgical adhesive comprising the composition of claim 4.

25. A surgical sealant comprising the composition of claim 4.

26. The biocompatible monomer composition of claim 4, wherein the monomer is an alkoxyalkyl cyanoacrylate monomer.

27. A biocompatible monomer composition according to claim 4, wherein said biocompatible pH modifier is thoroughly mixed with said at least one monomer.

28. A biocompatible composition, comprising:
   (a) a polymer whose in vivo biodegradation produces formaldehyde; and
   (b) an effective amount of at least one biocompatible pH modifier to modify the pH of an immediate environment of the biocompatible composition in situ to a pH range at which the polymer's in situ biodegradation proceeds at a rate different than at physiologic pH,
   wherein said pH modifier is in at least one form selected from the group consisting of:
      (a) insoluble in monomer from which said polymer is formed,
      (b) in a microcapsule,
      (c) chemically protected and insoluble in the monomer,
      (d) chemically protected and basic,
      (e) acidic and chemically protected form of at least one member selected from the group consisting of amino acids; di-acids and salts thereof; polyacids and salts thereof; esters that are easily hydrolyzable in vivo; lactones that are easily hydrolyzable in vivo; organic carbonates; enolic compounds; acidic phenols; polyphenolic compounds; aromatic alcohols; boron-containing compounds; sulfonic acids and salts thereof; sulfinic acids and salts thereof; phosphorus-containing compounds; acid halides; chloroformates; acid gases; acid anhydrides; inorganic acids and salts thereof; and polymers having functional groups of at least one member selected from the group consisting of amino acids, di-acids and salts thereof, polyacids and salts thereof, lactones that are easily hydrolyzable in vivo, organic carbonates, enolic compounds, acidic phenols, polyphenolic compounds, aromatic alcohols, boron-containing compounds, sulfonic acids and salts thereof, sulfinic acids and salts thereof, phosphorus-containing compounds, acid halides, chloroformates, acid gases, acid anhydrides, and inorganic acids and salts thereof, and
      (f) acidic and chemically protected form of at least one member selected from the group consisting of D-galacturonic acid; succinic acid and succinic anhydride; glycolic acid; poly(acrylic acid); acetic acid; diglycolic ahyhdride; citraconic anhydride; maleic anhydride; diethyl oxalate; Meldrum's acid; diethyl carbonate; dipropyl carbonate; diethyl pyrocarbonate; diallyl pyrocarbonate; di-tert-butyl dicarbonate; ascorbic acid; catechin; D-glucosamine hydrochloride; 4-hydroxyephedrin hydrochloride; boric acid; nitric acid; hydrochloric acid; sulfuric acid; ethanesulfonic acid; p-toluenesulfonic acid; 2-aminoethylphosphoric acid; methylphosphonic acid; dimethylphosphinic acid; methyl chloroformate; sulfur dioxide; carbon dioxide; and combinations of the above materials.

29. The composition of claim 28, wherein the pH modifier is a chemically protected acid.

30. The composition of claim 28, wherein the pH modifier is a base or anhydrous precursor thereof or a chemically protected base.

31. The composition of claim 28, wherein the polymer is formed in vivo.

32. The composition of claim 28, wherein the polymer is formed ex vivo.

33. The composition of claim 28, wherein the polymer can biodegrade at a physiologic pH and the pH modifier is an acid or anhydrous precursor thereof or a chemically protected acid.

34. The composition of claim 28, wherein the polymer biodegrades slowly or not at all at physiologic pH and the pH modifier is a base or anhydrous precursor thereof or a chemically protected base.

35. The composition of claim 28, further comprising at least one biocompatible agent effective to reduce active formaldehyde concentration levels.

36. A delivery system for a therapeutic agent, comprising:
    (a) a suitable carrier or matrix comprising the composition of claim 28; and
    (b) a therapeutic agent deposited on or within the carrier or matrix.

37. A cross-linked monomer surgical implant molded from the composition of claim 28 comprising;
    (a) at least one cross-linking agent, and
    (b) said composition of claim 28.

38. The implant of claim 37, comprising a prosthetic device.

39. The implant of claim 38, comprising a tissue fastener.

40. The biocompatible composition of claim 28, wherein the monomer is a 1,1-disubstituted ethylene monomer.

41. The biocompatible composition of claim 28, wherein the monomer is an alkoxyalkyl cyanoacrylate monomer.

42. A method of regulating a rate of in vivo biodegradation of a polymer formed in vivo from at least one monomer that forms a polymer at a physiologic pH, comprising:
    combining said at least one monomer with (1) an effective amount of at least one biocompatible pH modifier to modify a pH of an immediate in situ environment of the polymer to a pH range at which the polymer's biodegradation proceeds at a different rate than it does at physiologic pH and (2) at least one thickening agent different from said pH modifier;
    allowing the polymer to form in vivo; and
    maintaining the thus-formed polymer in vivo for a time sufficient to effect biodegradation of the polymer,
    wherein said pH modifier is insoluble in the monomer, or in a microcapsule or chemically protected form.

43. The method of claim 40, wherein said thickening agent is at least one member selected from the group consisting of polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylate and butadiene.

44. A biocompatible monomer composition, comprising:
    (a) at least one monomer comprised of a 1,1-disubstituted ethylene, which forms a polymer in vivo at a physiologic pH;
    (b) an effective amount of a biocompatible pH modifier to regulate, after in vivo polymerization of the monomer in situ, the pH of an immediate in vivo environment of the polymer to a pH range at which the polymer biodegrades in vivo at a different rate than it does at physiologic pH, without significantly affecting in situ polymerization of the monomer; and
    (c) at least one thickening agent different from said pH modifier,
    wherein said pH modifier is insoluble in the monomer, or in a microcapsule or chemically protected form.

45. The composition of claim 44, wherein said thickening agent is at least one member selected from the group consisting of polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylate and butadiene.

46. A biocompatible composition, comprising:
    (a) a polymer whose in vivo biodegradation produces formaldehyde;
    (b) an effective amount of at least one biocompatible pH modifier to modify the pH of an immediate environment of the biocompatible composition in situ to a pH range at which the polymer's in situ biodegradation proceeds at a rate different than at physiologic pH; and
    (c) at least one thickening agent different from said pH modifier,
    wherein said pH modifier is insoluble in the monomer, or in a microcapsule or chemically protected form.

47. The composition of claim 46, wherein said thickening agent is at least one member selected from the group consisting of polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylate and butadiene.

48. A method of regulating a rate of in vivo biodegradation of a polymer formed in vivo from at least one monomer that forms a polymer at a physiologic pH, comprising:
    combining said at least one monomer with an effective amount of at least two different biocompatible pH modifiers having different release rates to modify a pH of an immediate in situ environment of the polymer to a pH range at which the polymer's biodegradation proceeds at a different rate than it does at physiologic pH;
    allowing the polymer to form in vivo; and
    maintaining the thus-formed polymer in vivo for a time sufficient to effect biodegradation of the polymer,
    wherein said pH modifiers are insoluble in the monomer, or in a microcapsule or chemically protected form.

49. A biocompatible monomer composition, comprising:
(a) at least one monomer comprised of a 1,1-disubstituted ethylene monomer, which forms a polymer in vivo at a physiologic pH; and
(b) an effective amount of at least two biocompatible pH modifiers having different release rates to regulate, after in vivo polymerization of the monomer in situ, the pH of an immediate in vivo environment of the polymer to a pH range at which the polymer biodegrades in vivo at a different rate than it does at physiologic pH, without significantly affecting in situ polymerization of the monomer,
wherein said pH modifiers are insoluble in the monomer, or in a microcapsule or chemically protected form.

50. A biocompatible composition, comprising:
(a) a polymer whose in vivo biodegradation produces formaldehyde; and
(b) an effective amount of at least two biocompatible pH modifiers having different release rates to modify the pH of an immediate environment of the biocompatible composition in situ to a pH range at which the polymer's in situ biodegradation proceeds at a rate different than at physiologic pH,
wherein said pH modifiers are insoluble in the monomer, or in a microcapsule or chemically protected form.

* * * * *